United States Patent

Stähle et al.

[11] 4,293,564
[45] Oct. 6, 1981

[54] 2-(3,5-DIBROMO-4-AMINO-PHENYLIMINO)-IMIDAZOLIDINE, SALTS AND COMPOSITIONS THEREOF

[75] Inventors: Helmut Stähle; Herbert Köppe; Werner Kummer, all of Ingelheim am Rhein; Wolfgang Hoefke, Budenheim; Wolfram Gaida, Ingelheim am Rhein, all of Fed. Rep. of Germany; Ludwig Pichler, Vienna, Austria

[73] Assignee: Boehringer Ingelheim GmbH, Ingelheim, Fed. Rep. of Germany

[21] Appl. No.: 179,839

[22] Filed: Aug. 20, 1980

Related U.S. Application Data

[63] Continuation-in-part of Ser. No. 12,650, Feb. 16, 1979, Pat. No. 4,250,186.

[30] Foreign Application Priority Data

Feb. 17, 1978 [DE] Fed. Rep. of Germany ....... 2806775

[51] Int. Cl.³ .................. A61K 31/415; C07D 233/50
[52] U.S. Cl. ................................. 424/273 R; 548/315
[58] Field of Search ................... 548/315; 424/273 R

[56] References Cited

U.S. PATENT DOCUMENTS 3,468,887 9/1969 Stahle et al. ...................... 424/273

*Primary Examiner*—Henry R. Jiles
*Assistant Examiner*—R. W. Ramsuer
*Attorney, Agent, or Firm*—Hammond & Littell, Weissenberger & Muserlian

[57] ABSTRACT

The compound of the formula

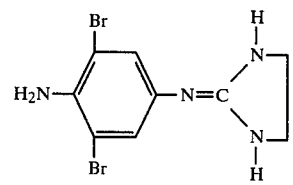

and non-toxic, pharmacologically acceptable acid addition salts thereof. The compound as well as its salts are useful as bradycardiacs.

2 Claims, No Drawings

2-(3,5-DIBROMO-4-AMINO-PHENYLIMINO)-IMIDAZOLIDINE, SALTS AND COMPOSITIONS THEREOF

This is a continuation-in-part of copending application Ser. No. 12,650, filed Feb. 16, 1979 now U.S. Pat. No. 4,250,186.

This invention relates to the novel compound 2-(3,5-dibromo-4-amino-phenylimino)-imidazolidine and non-toxic acid addition salts thereof, as well as to methods of preparing these compounds, pharmaceutical compositions containing them as active ingredients, and methods of using them as bradycardiacs.

THE PRIOR ART

Because of their oustanding pharmacological and therapeutic properties, 2-phenylimino-imidazolidines have for a long time commanded strong interest in the pharmaceutical industry. Therefore, compounds of this type have often been reported in the literature and are disclosed, for example in Belgian Pat. Nos. 623,305; 653,933; 687,656; 687,657 and 705,944. These prior disclosures also describe the principal methods for the preparation of 2-phenyliminoimidazolidines.

More particularly, the present invention relates to the novel compound of the formula

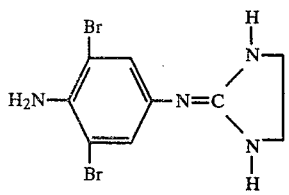

and non-toxic, pharmacologically acceptable acid addition salts thereof.

The compound of the formula I may be prepared by reacting a compound of the formula

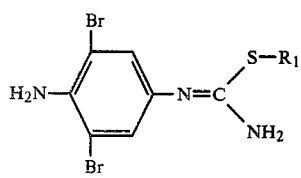

wherein $R_1$ is hydrogen or alkyl of 1 to 4 carbon atoms, or an acid addition salt thereof, with ethylenediamine or an acid addition salt thereof.

The reaction is performed at temperatures between 0° and 200° C., with or without a solvent. Polar protic, polar aprotic or non-polar solvents may be used. If the reaction is performed without a solvent, elevated temperatures should be applied. The reaction time depends upon the reactivity of the reactants and varies between a few minutes and several hours.

The starting compounds of the formula II may be obtained by converting a corresponding aniline with isothiocyanate into the analogous isothiourea, converting the latter with an alkylating agent into an isothiouronium salt, and treating this acid addition compound with a base to form the desired isothiourea compound.

The compounds embraced by formula I above are organic bases and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular example given below.

EXAMPLE 1

2-(4-Amino-3,5-dibromo-phenylimino)-imidazolidine and its hydrochloride by method A A mixture of 30.35 gm (0.065 mol) of 2-(4-amino-3,5-dibromo-phenyl)-S-methyl-isothiouronium hydroiodide, 6.5 mol of ethylenediamine and 65 ml of methanol was refluxed for 10 hours. Thereafter, the methanol was evaporated in vacuo, and the viscous residue was dissolved in methanol. The solution was filtered, and the filtrate was made alkaline with aqueous 50% potassium hydroxide while adding ice, whereby a precipitate formed which crystallized upon being stirred with ether, yielding 2-(4-amino-3,5-dibromo-phenylimino)-imidazolidine base, m.p. 152°–153° C.

The base was dissolved in a little methanol, the solution was acidified with ethereal hydrochloric acid until acid to Congo red, and ether was added. The precipitate formed thereby was collected and dried, yielding 3.20 gm (13.3% of theory) of the hydrochloride, m.p. 234°–236° C., $R_f$-value 0.4 in mobile phase 50 parts benzene, 40 parts dioxane, 5 parts ethanol, 5 parts concentrated ammonium hydroxide. Carrier: silicagel, visualization: ultraviolet light and potassium iodoplatinate.

The compound of the present invention, that is, that of the formula I and its non-toxic, pharmacologically acceptable acid addition salts, have useful pharmacodynamic properties. More particularly, they exhibit strong bradycardiac activity in warm-blooded animals, such as rabbits and cats, and are therefore useful for the treatment of coronary disorders.

The bradycardiac properties of 2-(3,5-dibromo-4-amino-phenylimino)-imidazolidine (A) and of a closely realted known compound, 2-(3′,5′-dichloro-4′-amino-phenylamino)-1,3-diazacyclopentene-(2) generically disclosed in U.S. Pat. No. 3,468,887 (B), were tested on groups of 5 adult laboratory rabbits having a body weight of 2.5 to 3 kg under urethane anesthesia. The heart rate of the test animals was continuously recorded before and after i.v. administration of the test compound, and the maximum variation in this parameter was observed.

The following table shows the results obtained:

| Compound | Dose mgm/kg | Max. effect on heart rate beats/min. |
|---|---|---|
| Invention: | | |
| A | 1 | −202 |
| | 0.1 | −90 |
| Prior art: | | |

-continued

| Compound | Dose mgm/kg | Max. effect on heart rate beats/min. |
|---|---|---|
| B | 1 | −122 |
| | 0.1 | −30 |

The values tabulated above clearly show that compound A is a significantly more effective bradycardiac than the nearest prior art compound B.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compound according to the present invention is from 0.0016 to 1.33 mgm/kg body weight, preferably 0.0083 to 0.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 2

Tablets

The tablet composition is compounded from the following ingredients:

| | |
|---|---|
| 2-(3,5-Dibromo-4-amino-phenylimino)-imidazolidine hydrobromide | 5 parts |
| Lactose | 65 parts |
| Corn starch | 130 parts |
| Sec. calcium phosphate | 40 parts |
| Soluble starch | 3 parts |
| Magnesium stearate | 2 parts |
| Colloidal silicic acid | 4 parts |
| Total | 250 parts |

Preparation:

The active ingredient is admixed with a portion of all of the excipients, the mixture is moistened with an aqueous solution of the soluble starch, the moist mass is granulated by passing it through a screen, and the granulate is dried. The dry granulate is admixed with the remainder of the excipients, and the composition is compressed into 250 mgm-tablets. Each tablet is an oral dosage unit composition containing 5 mgm of the active ingredient.

EXAMPLE 3

Hypodermic solution

The solution is compounded from the following ingredients:

| | | |
|---|---|---|
| 2-(3,5-Dibromo-4-amino-phenylimino)-imidazolidine hydrobromide | | 1.0 parts |
| Sodium chloride | | 18.0 parts |
| Distilled water | q.s.ad | 2000.0 parts by vol. |

Preparation:

The active ingredient and the sodium chloride are dissolved in the distilled water, and the solution is filled under aseptic conditions and in an atmosphere of nitrogen into 2 cc-capsules which are subsequently sterilized and sealed. The contents of each ampule are an injectable dosage unit composition containing 1 mgm of the active ingredient.

EXAMPLE 4

Drop solution

The solution is compounded form the following ingredients:

| | | |
|---|---|---|
| 2-(3,5-Dibromo-4-amino-phenylimino)-imidazolidine hydrobromide | | 0.02 parts |
| Methyl p-hydroxy-benzoate | | 0.07 parts |
| Propyl p-hydroxy-benzoate | | 0.03 parts |
| Demineralized water | q.s.ad | 100.0 parts by vol. |

Preparation:

The active ingredient and the p-hydroxy-benzoates are dissolved in the demineralized water. 5 ml (20 drops) of the solution are an oral dosage unit composition containing 1 mgm of the active ingredient.

The free base or any other non-toxic, pharmacologically acceptable acid addition salt thereof may be substituted for the particular active ingredient in Examples 2 through 4. Likewise, the amount of active ingredient in these illustrative examples may be varied to achieve the dosage unite range set forth above, and the amounts and nature of the inert pharmacological carrier ingredients may be varied to meet particular requirements.

We claim:

1. 2-(3,5-Dibromo-4-amino-phenylimino)imidazolidine or a non-toxic, pharmacologically acceptable acid addition salt thereof.

2. A bradycardiac pharmaceutical dosage unit composition consisting essentially of an inert pharmaceutical carrier and an effective bradycardiac amount of a compound of claim 1.

* * * * *